US008759351B2

(12) United States Patent
Brown

(10) Patent No.: US 8,759,351 B2
(45) Date of Patent: *Jun. 24, 2014

(54) METHODS FOR ADMINISTERING ARIPIPRAZOLE

(71) Applicant: Alkermes, Inc., Waltham, MA (US)

(72) Inventor: Josiah Brown, Seattle, WA (US)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/648,544

(22) Filed: Oct. 10, 2012

(65) Prior Publication Data

US 2013/0090343 A1    Apr. 11, 2013

Related U.S. Application Data

(63) Continuation of application No. 12/251,656, filed on Oct. 15, 2008, now Pat. No. 8,338,427, which is a continuation of application No. 10/635,221, filed on Aug. 6, 2003, now abandoned.

(51) Int. Cl.
*A61K 31/445* (2006.01)
*A61K 31/497* (2006.01)
*A61K 9/00* (2006.01)

(52) U.S. Cl.
USPC ............... 514/253.07; 514/327; 514/252.13; 514/253.01; 424/400

(58) Field of Classification Search
USPC ............ 514/253.07, 327, 252.13, 253.01; 424/400
See application file for complete search history.

(56) References Cited

U.S. PATENT DOCUMENTS

| 5,006,528 | A  | * | 4/1991  | Oshiro et al. | 514/253.07 |
| 6,987,111 | B2 | * | 1/2006  | Greco et al.  | 514/220    |
| 7,658,998 | B2 | * | 2/2010  | Brown et al.  | 428/403    |
| 8,338,427 | B2 | * | 12/2012 | Brown         | 514/253.07 |
| 8,338,428 | B2 | * | 12/2012 | Brown         | 514/253.07 |

OTHER PUBLICATIONS

Floyd and Jain, Chapter 7: Injectable Emulsions and Suspensions, in Pharmaceutical Dosage Forms: Disperse Systems, vol. 2, 2nd ed. H.A. Lieberman et al. eds., p. 288-301.*
Remington's, 1985, Mack Publishing Company, p. 659.*
Remington's, 1990, Mack Publishing Company, pp. 1676-1693.*

* cited by examiner

*Primary Examiner* — Abigail Fisher
(74) *Attorney, Agent, or Firm* — Cooley LLP

(57) ABSTRACT

The present invention relates, in part, to the discovery that a pharmaceutical composition comprising aripiprazole and a carrier administered in a bolus injection resulted in an extended release profile similar to that obtained by the injection of a poly lactide-co-glycolide microsphere formulation containing the active agent. This surprising result suggests that pharmacologically beneficial extended release formulations without the complexities and expense associated with the manufacture microspheres.

2 Claims, 1 Drawing Sheet

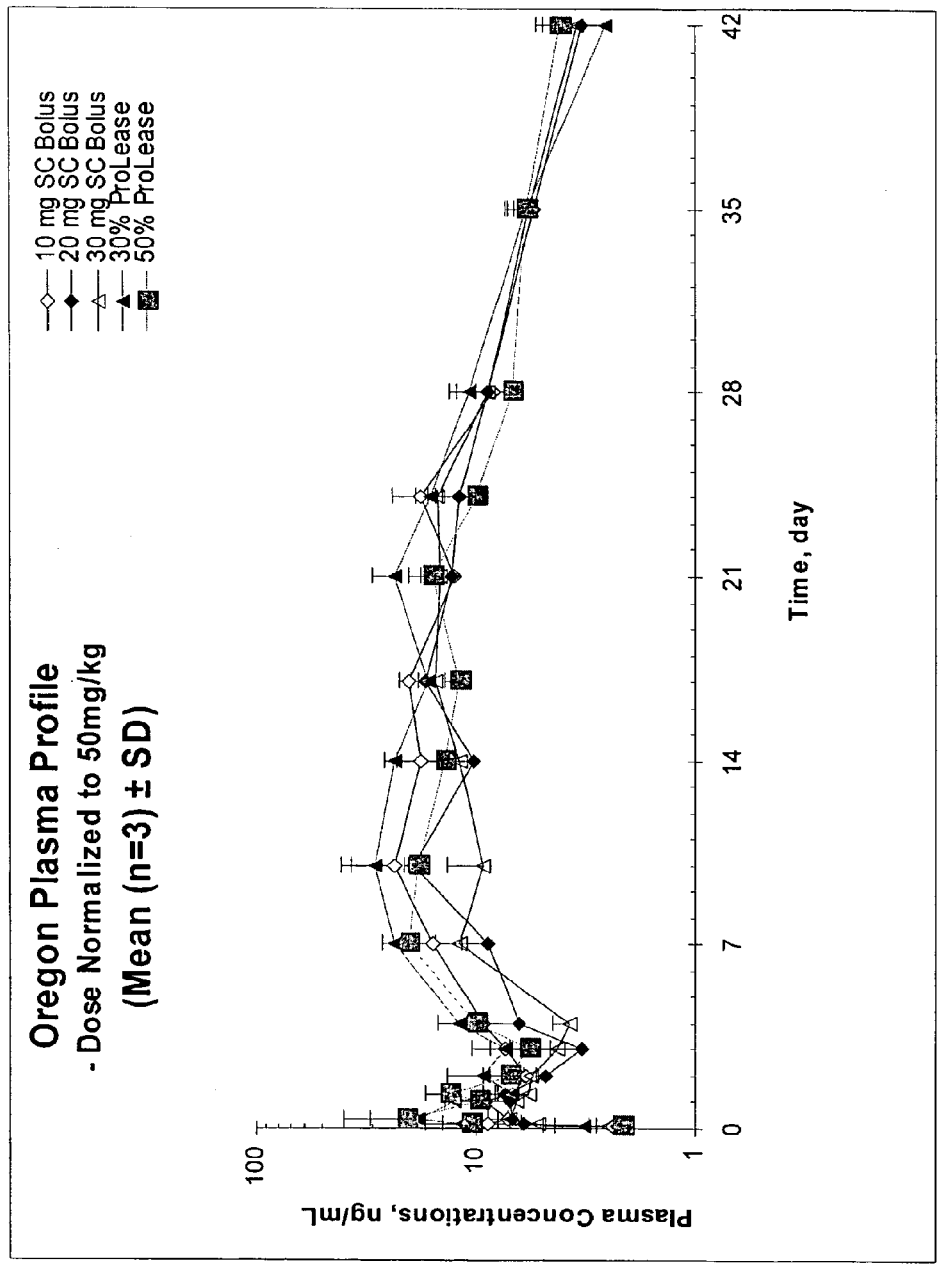

US 8,759,351 B2

METHODS FOR ADMINISTERING ARIPIPRAZOLE

RELATED APPLICATION

This application is a continuation of U.S. application Ser. No. 12/251,656, filed Oct. 15, 2008 which is a continuation of U.S. application Ser. No. 10/635,221, filed Aug. 6, 2003, now abandoned. The entire teaching of the above application is incorporated herein by reference.

BACKGROUND OF THE INVENTION

Aripiprazole, sold under the tradename ABILIFY®, is a dopamine $D_2$ and serotonin 5-$HT_{1A}$ receptor agonist and antagonist of the serotonin 5-$HT_{2A}$ receptor. Aripiprazole is used to treat schizophrenia and other psychotic and CNS disorders. See U.S. Pat. No. 5,006,528, for example. ABILIFY®, is currently sold as a tablet for oral administration. However, poor patient compliance with oral antipsychotics has been reported. As such, there exists a need for improved methods of delivering antipsychotics, such as aripiprazole, thereby improving patient compliance and maximizing the pharmacological profile of the active agent.

SUMMARY OF THE INVENTION

The present invention relates, in part, to the discovery that a pharmaceutical composition comprising aripiprazole and a carrier administered in a bolus injection resulted in an extended release profile similar to that obtained by the injection of a poly lactide-co-glycolide microsphere formulation containing the active agent. This surprising result suggests that pharmacologically beneficial extended release formulations without the complexities and expense associated with the manufacture of polymeric microspheres can be achieved.

Thus, the invention relates to an injectable composition for the extended release of aripiprazole comprising injecting or implanting a composition comprising aripiprazole wherein aripiprazole is present in the serum of the mammal for at least about 7 days, preferably at least about 14 days, more preferably at least about 21 days, such as about three months. In a preferred embodiment, the composition comprises a suspension of aripiprazole in an injection vehicle, such as a suspension of an aripiprazole drug substance in an injection vehicle. The aripiprazole drug substance can comprise, consist essentially of or consist of aripiprazole (in a crystalline, non-crystalline or amorphous form), an aripiprazole salt, an aripiprazole solvate (including hydrates), or other aripiprazole polymorphs. The aripiprazole, or aripiprazole drug substance, can be added in a specified size. For example, the aripiprazole or aripiprazole drug substance can be added after being micronized to a mass mean diameter of less than about 100 microns, preferably between about 30 and 80 microns, as determined by Coulter counter.

In one embodiment, the aripiprazole or aripiprazole drug substance is injected as a mixture (including a suspension) of at least about 50 mg aripiprazole in an injection vehicle, such as at least about 70 to 210 mg or as much as about 900 to 2700 mg, e.g. less than 5400 mg. The aripiprazole can be present in an amount of at least about 10 mg/ml, preferably at least about 20 mg/ml or at least about 30 mg/ml. The invention also relates to methods for providing aripiprazole to an individual in an extended release injectable composition comprising administering a mixture of at least about 10 mg/ml aripiprazole in an injection vehicle comprising a viscosity enhancing agent and to compositions useful in such methods.

BRIEF DESCRIPTION OF THE DRAWINGS

The FIGURE compares the release profiles of subcutaneous injections (SC Bolus) according to the invention with injections of aripiprazole-containing microspheres.

DETAILED DESCRIPTION OF THE INVENTION

The invention relates to an injectable composition for the extended release of aripiprazole comprising a mixture of aripiprazole in an injection vehicle comprising an optional viscosity enhancing agent. The aripiprazole can be present in an amount of at least about 10 mg/ml, preferably at least about 20 mg/ml or at least about 30 mg/ml. The invention also relates to methods for providing aripiprazole to an individual in an extended release injectable composition comprising administering a mixture of at least about 50 mg aripiprazole in an injection vehicle.

In general, the aripiprazole will be suspended in the injection vehicle. In one embodiment, the aripiprazole is supplied in a free flowing powder, substantially free of major amounts of pharmaceutical excipients or other compounds. For example, the aripiprazole can be supplied in a micronized state, consisting of or consisting essentially of aripiprazole. An aripiprazole drug substance can be said to consist essentially of aripiprazole if it contains, for example, 90% by weight or more aripiprazole and minor amounts (e.g., less than 10% by weight) of other materials that are, for example, residual to its process for manufacture. Compounds that may be found in a substantially pure aripiprazole drug substance can include wetting agents used, for example, to facilitate micronization, grinding or comminution, residual solvents, reaction by products or staring materials.

The compositions of the present invention are free of sustained release matrices. Sustained release matrices are polymers and other macromolecules (albumin), present in major amounts (e.g., 50% by weight or more of total solids), which when the active agent is dispersed therein, are used to slow the exposure or bioavailability of the active agent in the patient. A frequently used polymeric matrix is poly lactide-co-glycolide polymers. Thus, the aripiprazole drug substance and/or injectable compositions of the invention generally do not contain major amounts of PLGA polymer matrices.

Of course, polymers are often found in pharmaceutical compositions where the activity is not at all related to extending the release profile of the drug. For example, minor amounts of polysorbates, polyamines, polyvinylalcohol and polyethylene glycols are added to facilitate dispersibility of active agents in its vehicles. The inclusion of such polymers in amounts intended to accomplish these functions, and in amounts that do not permit the formation of substantial matrix formation, is permitted.

The aripiprazole drug substance is added to an injection vehicle. The drug substance can be dispersed or suspended in the vehicle, depending upon the solubility of the drug in the vehicle. The vehicle is preferably an aqueous vehicle which suspends the drug substance. Preferably, the vehicle contains a viscosity enhancing agent.

Viscous vehicles can have, for example, a viscosity of at least 20 cp at 20° C. In other embodiments, the fluid phase of the suspension has a viscosity at 20° C. of at least about 30 cp, 40 cp, 50 cp, and 60 cp are preferred. The viscosity can be achieved by adding a viscosity enhancing agent, such as a carboxymethyl cellulose, such as sodium carboxy methylcellulose. In one embodiment, the injection vehicle comprises at least about 1% by volume sodium carboxymethyl cellulose, preferably about 3% by volume carboxymethyl cellulose.

The injection vehicle can advantageously contain a wetting agent, such as a polysorbate. Suitable polysorbates include polysorbate 20, polysorbate 40, and polysorbate 80, sold under the trademark TWEEN®. The wetting agent can be added in an amount that enhances the dispersibility of the active agent. An example of a suitable amount includes about 0.1 to 2% by weight of polysorbate 20.

The injection vehicle can also advantageously employ a density enhancing agent, such as a sugars, e.g. mannitol, or sorbitol and/or a tonicity adjusting agent, such as sodium chloride. In one embodiment, the tonicity adjusting agent is about 1% by weight, including 0.9% by weight.

In one embodiment, the composition consists of the aripiprazole drug substance and the injection vehicle, thereby providing a surprisingly simple and elegant formulation for obtaining an extended or sustained release profile.

The aripiprazole drug substance can comprise, consist essentially of or consist of aripiprazole (in a crystalline, non-crystalline or amorphous form), an aripiprazole salt, an aripiprazole solvate (including ethanolates and hydrates), or other aripiprazole polymorphs. Preferred salts include those salts insoluble in an aqueous vehicle. Pharmaceutical salts such as the hydrochloride and hydrobromide salts are suitable.

The methods of the invention include administering the compositions described herein, thereby obtaining an extended release or sustained release profile in the patient. An extended release profile includes deliveries that achieve a therapeutically effective amount of the aripiprazole is present in the plasma of the individual for at least about 7 days, preferably at least about 14 days, or more preferably at least about 21 days alternatively for at least 2, 3, 4, 6 or 8 weeks or as much as three months.

In one embodiment, the formulations can be administered as a single or sole dose. However, the invention is particularly beneficial for those individuals that require constant or chronic therapy, such as those that receive repeated doses over several weeks or months or more. In such dosing regimens, the method can comprise a first administration of a first extended release formulation and a second administration of a second extended release formulation. The second formulation can be the same, substantially the same or different as the first and can include the same active agent or a different active agent. For example, the second formulation can be administered at about 7 days, or more, such as at least about 14 days, or at least about 17 days, after the first administration, where the first administration results in the release of agent for a period of 1, 2, 3, 4, 5, 6, 7, 8, 9, 10, 11, 12, 13, 14 days, or more.

The term "therapeutically effective amount" is further meant to define an amount resulting in the improvement of any parameters or clinical symptoms. The actual dose may vary with each patient and does not necessarily indicate a total elimination of all disease symptoms.

As used herein, the term "individual", "subject" or "patient" refers to a warm blooded animal, including but not limited to humans, such as a mammal which is afflicted with a particular disease state.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

The mode of administration will generally be by injection or implantation, such as intramuscularly or subcutaneously.

Preferred amounts according to the selected mode of administration are able to be determined by one skilled in the art. Pharmaceutical compositions can be manufactured utilizing techniques known in the art. Typically the therapeutically effective amount of the compound will be admixed with a pharmaceutically acceptable carrier.

For injection, the compounds may be in a physiologically acceptable pharmaceutical carrier and administered as a suspension. Illustrative pharmaceutical carriers also include water, aqueous methylcellulose solutions, saline, dextrose solutions, fructose solutions, ethanol, or oils of animal, vegetative, or synthetic origin. The pharmaceutical carrier may also contain preservatives, and buffers as are known in the art.

When the composition is to be used as an injectable material, including but not limited to needle-less injection, it can be formulated into a conventional injectable carrier. Suitable carriers include biocompatible and pharmaceutically acceptable solutions.

In a preferred embodiment, the size of the drug particle can be controlled. Often, the mass mean diameter of the drug particles is less than 100 microns, such as between about 1 and 100 microns, preferably about 10 and 100 microns, or about 20 and 60 microns.

In one embodiment, the unit dosage form can be stored as a dry powder, for example, to be mixed for injection prior to use, or as a stable suspension ready for use. Other methods for storing or administration using art recognized methods are also contemplated herein.

EXPERIMENTAL

Pharmacokinetic Evaluation of Aripiprazole in Rats Following Administration of Single Subcutaneous Doses of Aripiprazole Formulations Species and Strain: Sprague-Dawley rats. Male; 450+/−50 grams.
Study Groups: 5 Groups, 15 subjects
    Group A: three rats injected once SC with 10 mg of Aripiprazole.
    Group B: three rats injected once SC with 20 mg of Aripiprazole.
    Group C: three rats injected once SC with 30 mg of Aripiprazole.
    Group D: three rats injected once SC with ~67 mg of microparticles.
    Group E: three rats injected once SC with ~40 mg of microparticles.

| Group Conditions Table: | | | | |
|---|---|---|---|---|
| Rat Groups | Lot # | Polymer | Notes | % Load |
| A | | N/A | Bulk Drug | 100% |
| B | | N/A | Bulk Drug | 100% |

-continued

Group Conditions Table:

| Rat Groups | Lot # | Polymer | Notes | % Load |
|---|---|---|---|---|
| C | | N/A | Bulk Drug | 100% |
| D | 03-10-66-B | 4A | Bulk Drug in microspheres | 30% |
| E | 03-10-66-C | 4A | Bulk Drug in microspheres | 50% |

Route of Injection: Subcutaneous (SC) injection into the interscapular region.

Injection Vehicle: Aqueous diluent containing 3% CMC (low viscosity), 0.1% Tween 20, in 0.9% NaCl and water.

Dose Volumes: Suspensions were formulated as follows:
 Group A: 10 mg powder in 0.75 mL Diluent
 Group B: 20 mg powder in 0.75 mL Diluent
 Group C: 30 mg powder in 0.75 mL Diluent
 Group D: ~67 mg microparticles in 0.75 mL Diluent
 Group E: 40 mg microparticles in 0.75 mL Diluent Blood Collection: Blood samples were collected via a lateral tail vein after anesthesia with Halothane. A syringe without an anticoagulant was used for the blood collection, then the whole blood was transferred to tubes containing K2 EDTA and mixing beads (MICROTAINER®; MFG# BD365974). The blood samples were processed (the tubes are inverted 15-20 times and centrifuged for 2 minutes at >14,000 g's) to separate plasma. The plasma samples prepared in this manner were transferred to labeled plain tubes (MICROTAINER®; MFG# BD5962) and stored frozen at <−70° C.

Blood Volumes: At least 250 µL blood were collected at for each time point during the first 24 hours and 400 µL for at each time point thereafter.

Time Points to obtain plasma:

| | | | | |
|---|---|---|---|---|
| 2 h | 24 h | 3 d | 10 d | 21 d |
| 4 h | 32 h | 4 d | 14 d | 24 d |
| 8 h | 2 d | 7 d | 17 d | 28 d |

Note:
when plasma concentration was lower than the limitation of quantification, that group of ats were terminated.

The results obtained are reported in the FIGURE. Surprisingly, the rats that received bolus injections of aripiprazole and injection vehicle alone were substantially the same as those that received the aripiprazole dispersed within a PLGA microsphere.

Modifications and variations of the invention will be obvious to those skilled in the art from the foregoing detailed description of the invention. Such modifications and variations are intended to come within the scope of the appended claims.

All patents, patent application publications and articles cited herein are incorporated by reference in their entirety.

I claim:

1. An injectable composition that is free of sustained release matrices for the extended release of aripiprazole comprising a suspension of at least about 10 mg/ml of aripiprazole in an injection vehicle optionally comprising a viscosity enhancing agent wherein the aripiprazole release is for at least 21 days.

2. A method for providing aripiprazole to an individual in an extended release injectable composition that is free of sustained release matrices comprising administering a mixture of at least about 10 mg/ml of aripiprazole in an injection vehicle optionally comprising a viscosity enhancing agent, wherein a therapeutically effective amount of the aripiprazole is present in the plasma of the individual for at least about 21 days.

* * * * *